United States Patent [19]

Black

[11] Patent Number: 4,990,140
[45] Date of Patent: Feb. 5, 1991

[54] FLEXIBLE SPRAY TIP FOR SYRINGE

[75] Inventor: John R. Black, Trenton, N.J.

[73] Assignee: Johnson & Johnson Medical, Inc., Arlington, Tex.

[21] Appl. No.: 435,855

[22] Filed: Nov. 13, 1989

[51] Int. Cl.⁵ .............................................. A61M 5/32
[52] U.S. Cl. .................................... 604/192; 604/239; 604/241; 604/263; 604/275; 604/281
[58] Field of Search ............... 604/188, 239–243, 604/263, 264, 275, 281, 282, 902, 192; 222/573

[56] References Cited

U.S. PATENT DOCUMENTS

| | | | |
|---|---|---|---|
| 3,169,528 | 2/1965 | Knox, III et al. | 604/281 |
| 3,439,675 | 4/1969 | Cohen | 604/192 |
| 4,044,765 | 8/1977 | Kline | 604/282 X |
| 4,402,684 | 9/1983 | Jessup | 604/264 |
| 4,405,308 | 9/1983 | Jessup | 604/200 |
| 4,547,193 | 10/1985 | Rydell | 604/282 |
| 4,596,564 | 6/1986 | Spetzler et al. | 604/281 |
| 4,767,416 | 8/1988 | Wolf et al. | 604/239 |
| 4,801,263 | 1/1989 | Clark | 433/90 |
| 4,834,709 | 5/1989 | Banning et al. | 604/170 |

*Primary Examiner*—C. Fred Rosenbaum
*Assistant Examiner*—Adam J. Cermak
*Attorney, Agent, or Firm*—Paul A. Coletti

[57] ABSTRACT

A flexible spray tip device is provided so that the user may bend and rigidly hold a spray tip at the end of a syringe. Alternately, the spray tip may be rotated around 360°, to provide orientation and angulation of the device while simultaneously attached to the syringe.

6 Claims, 3 Drawing Sheets

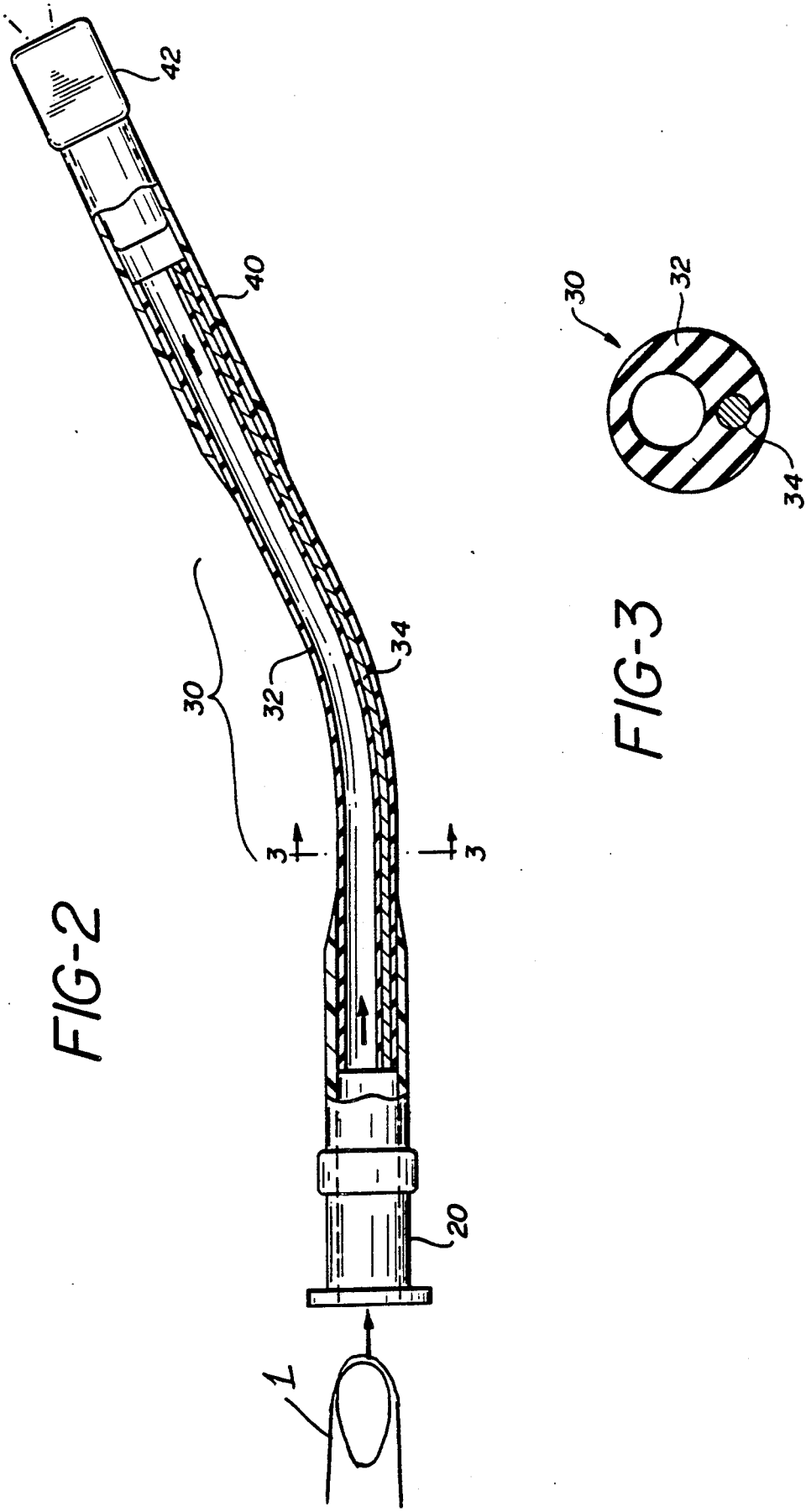

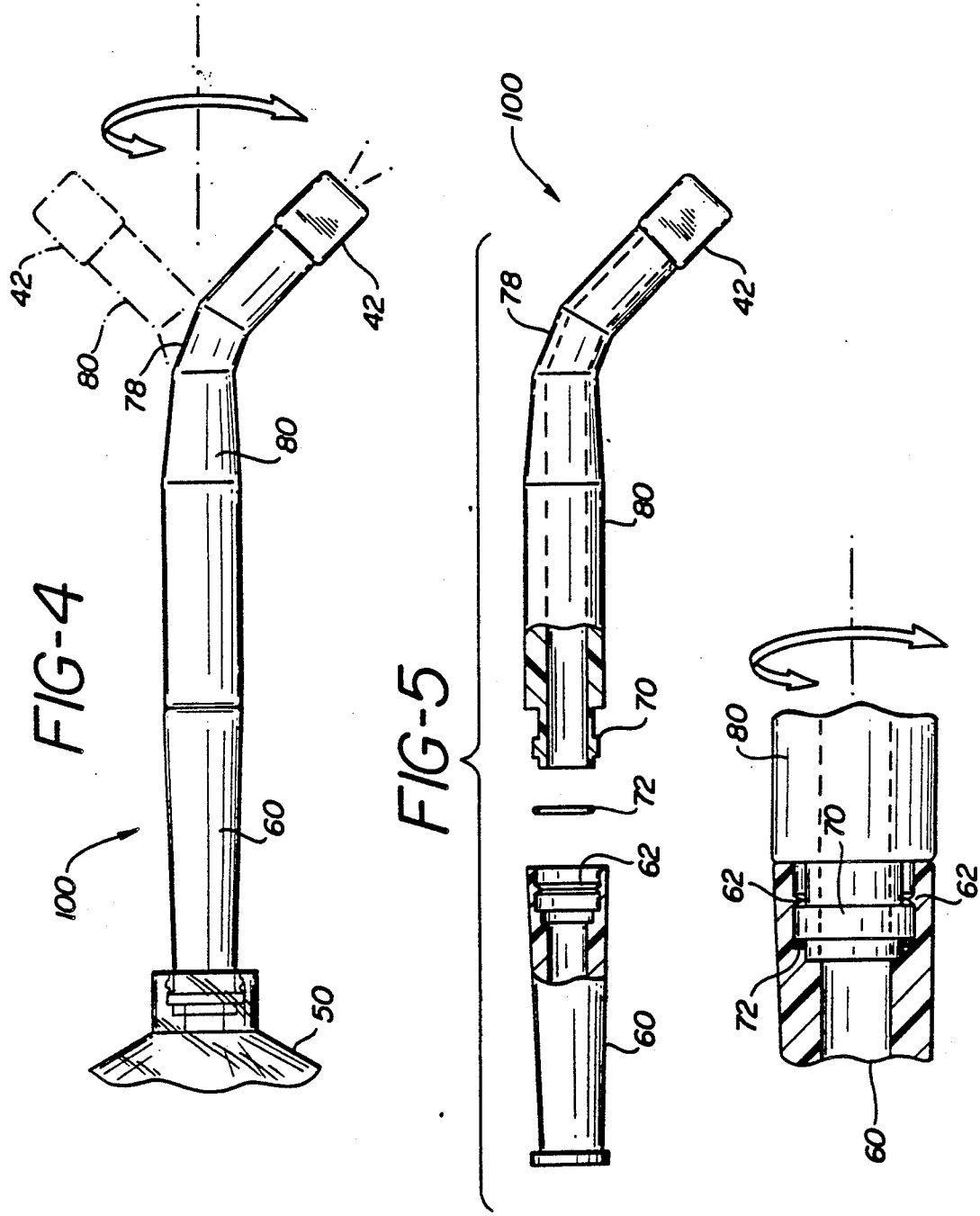

4,990,140

FLEXIBLE SPRAY TIP FOR SYRINGE

FIELD OF THE INVENTION

The invention relates generally to spray tips for syringes. More specifically, the invention relates to flexible spray tips used in conjunction with hypodermic syringes in the medical field. Most specifically, the invention relates to flexible and locking spray tips for use with hypodermic syringes in the medical field.

BACKGROUND OF THE INVENTION

Generally, hypodermic syringes have been in use for quite some time. These hypodermic syringes are useful in providing correct amounts of medication or fluid supplement to the body, or for drawing liquids such as blood from the body. In addition, syringes are useful in providing for topical treatment of medication to the skin.

In all previous uses, however, syringes have been configured so that in some instances it has been difficult to supply certain parts of the body. For instance, during surgery, if it is desired to apply topical treatment to an open surgical site, in some instances the syringe must be manipulated to be put near the site. Present syringes have been difficult to manipulate to provide treatment or draw different components from the site.

In some instances, flexible conduits have been provided to the syringe tip in order to make the syringe tip more pliable. In this way, it has been found that in some cases it is made easier to apply different reagents to the body.

In other instances, it has also been attempted to attach rigid extensions to the applicators on these syringes. In this way, it has been possible to provide reagents away from the vicinity of the wound site.

In none of these instances, however, has it been possible to manipulate the tip of the syringe from a removed position in order to accurately place the syringe tip at the wound site while simultaneously being able to manipulate the syringe tip. In this regard, it has also been impossible to manipulate the syringe tip to provide a spray device from the syringe at the wound site while maintaining the manipulability of the syringe tip and the spray device.

SUMMARY OF THE INVENTION

It is an object of the invention, therefore, to provide a spray tip for a syringe device where the tip is flexible and yet retains rigidity during actuation of the syringe.

It is further an object of the invention to provide a spray tip on a syringe where the syringe is able to be changed from one orientation to another.

It is further an object of the invention to provide a spray tip where the tip may be rotated through a number of orientations so that the user can comfortably determine the desired angulation of the spray tip.

These and other objects of the invention are found in the preferred embodiment of the device where a spray tip is connected to a flexible conduit. This flexible conduit contains a wire embedded in its inside wall so that the conduit remains fixed when shaped. Within the syringe device there is also provided a rotatable component so that the user cannot only flex the syringe tip, but orient the tip in any desired direction.

These and other aspects of the invention will be demonstrated in the accompanying figures and Detailed Description of the Invention.

DETAILED DESCRIPTION OF THE DRAWINGS

FIG. 2 is a cross-sectional elevational view of the invention;

FIG. 3 is a side elevational view of an alternate embodiment of the invention;

FIG. 4 is a cross-sectional view of the alternate embodiment of the invention; and FIG. 5 is an assembly view in partial cross-section of FIG. 4.

DETAILED DESCRIPTION OF THE INVENTION

Figure 1:
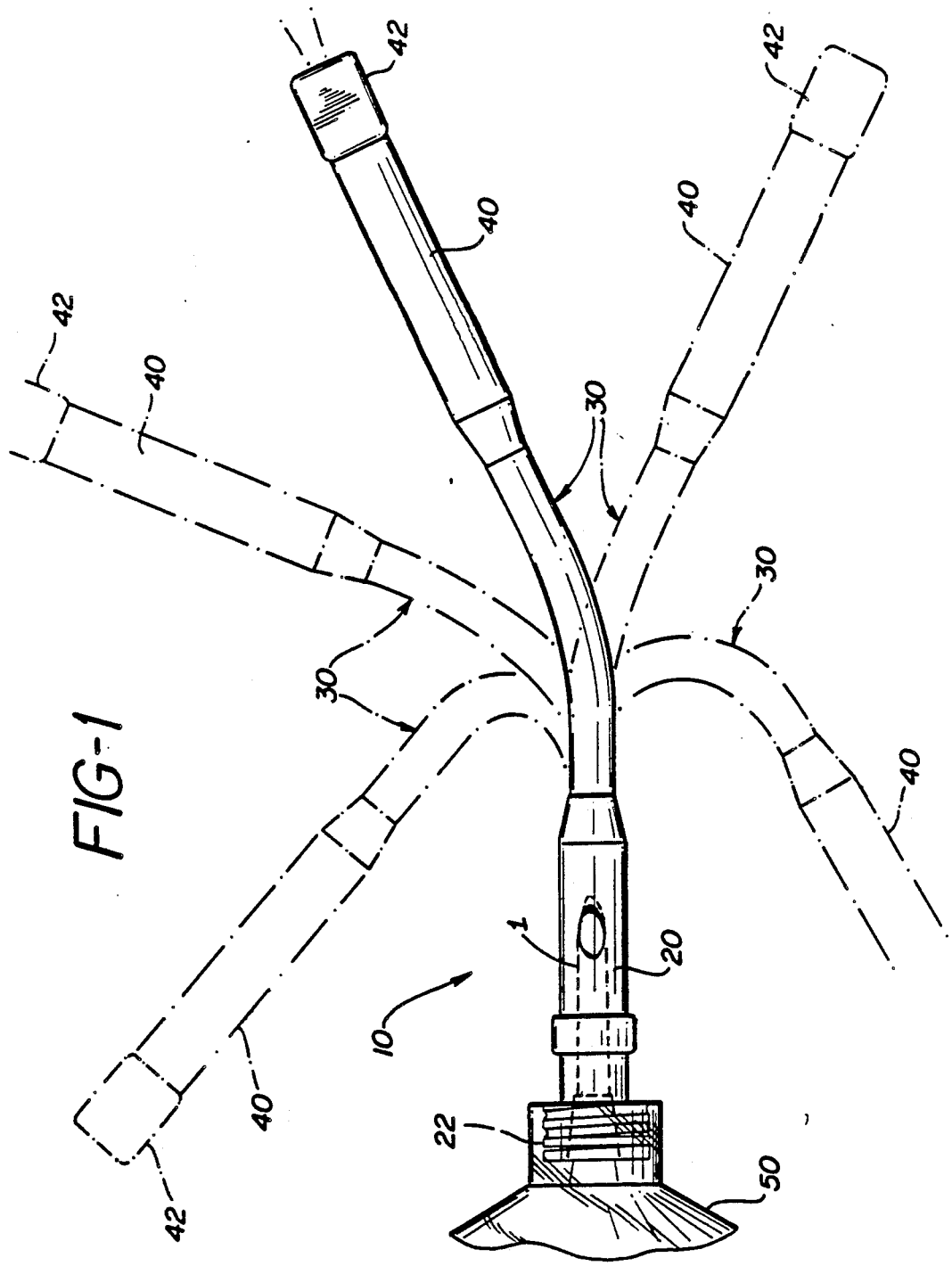
FIG. 1 is a side elevational view of a flexible spray device of the invention.

As seen from FIGS. 1 and 2, the invention comprises a flexible spray device 10 having a luer lock base 20, a bending area 30, a tip connector 40 and a spray tip 42. The luer lock base attaches to a syringe with a luer lock connection 22. The syringe 50 may either have a hypodermic needle 1 attached or unattached, as the luer lock base 22 easily adapts to attachment of the hypodermic needle. The spray tip 42 is a typical commercially available spray tip such as the spray tip manufactured by Calamar Inc. of Watchung, N.J.

The flexible bending area 30 comprises a flexible plastic tube 32 with a wire 34 embedded in the side wall of tube 32. The tube 32 is press fit into the luer lock base 22 and can be sealed with an adhesive or through welding. Because the tubing is flexible, it is bendable in any direction. Such examples of flexible tubing can be any flexible tubing made from vinyl, plastic, silicone, etc. In addition, the wire 34 cause the flexible plastic tube 32 to be rigid once the proper position is formed. Thus, the user is able to adjust and orient the spray tip device 10 in any desired direction, and then rely upon the spray tip 42 remain rigid during firing.

The tip connector 40 is formed from an injection molded rigid thermoplastic such as polypropylene or PVC. The flexible tubing 30 is press fit into the tip connector 40 and then sealed, much as bending area 30 is sealed to the luer lock base 22.

The spray tip 42 is press fit into the tip connector 40. The spray tip 42 is usually formed from a polypropylene liquid spray tip orifice, as those provided by Calamar, Inc.

Therefore, upon expressing any through the device, the flow through the tubing 32 is unobstructed with any flexing, bending or orienting of the device 10. The stainless steel wire 34 in the thermoplastic is able to fix the desired position when pressure is applied while expressing solution through the tubing 32. Therefore, the user is able to adjust the tubing to the proper orientation and then fire and express the fluids through the spray tip 42.

Alternately, as seen in FIGS. 4 and 5, the flexible tip can be provided with a 360° snap swivel connection 70. As seen in FIG. 4 or 5, attached to the luer lock base 20, instead of the flexible bending area 30, is 360° swivel connector 70. The luer lock 22 is formed to accept the snap swivel connector 70. The swivel connector 70 itself is injection molded thermoplastic such as polypropylene or PVC, etc. The rigid tubing section 72 of the 360° swivel connector is press fit into the luer lock base 22. The 360° snap swivel 74 locks into the base 72; snap swivel 74 may or may not contain O-ring 76 for sealing. The connection is made so that tubing section 74 stays rigid in luer lock base 22, and the swivel connector 74 fits over the rigidly connected tubing section 72, and can be rotated 360° during use. Either the flexible bending area 30 or spray tip 42 is press fit into the 360° swivel connector 70. Alternately, the end of the swivel connector 70 can have a fixed angle 78. The angle of the swivel connector 70 is generally formed at 30°. However, the angle may be fixed between 20° to 42° depending on requirements.

Thus with the alternate swivel connector 70 used in combination with flexible spry tip device 10, the user can orient the spray tip 42 at any angle and is able to at the same time rotate the device through any rotation. The improved device is therefore extremely adjustable, and is useful in any sort of procedure.

The present invention has been disclosed in connection with particularly preferred embodiments. It is to be understood, however, that the appended claims and their equivalents are meant to encompass the invention.

What is claimed is:

1. In combination:
a syringe containing a hypodermic needle; and
for attachment to said syringe, a bendable connector having a spray tip at one end, said connector having means for retaining said connector in a rigid position after bending and means for attachment to said syringe, said attachment means inserted over said hypodermic needle.

2. The combination of claim 1 wherein said retaining means comprises a wire embedded in said bendable connector.

3. The combination of claim 2 wherein said attachment means comprises a luer lock at one end for attachment to said syringe.

4. The combination of claim 3 wherein said connector attached to said syringe with said needle inserted into said luer lock attachment means.

5. The connector of claim 3 wherein said connector is formed from molded thermoplastic.

6. In combination:
a syringe containing a hypodermic needle; and
for attachment to said syringe containing a hypodermic needle, a connector having a luer lock end, said needle insertable into said luer lock end, a bendable plastic tube connected to said luer lock end, said tube containing a wire for maintaining said tube in a rigid position after bending, and a plastic spray tip connected to said bendable plastic tube.

* * * * *